(12) United States Patent
Yamamoto et al.

(10) Patent No.: US 7,696,530 B2
(45) Date of Patent: Apr. 13, 2010

(54) DUAL-GATE SENSOR

(75) Inventors: Tetsushi Yamamoto, Tokyo (JP); Tadahiko Hirai, Tokyo (JP); Shunji Imanaga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 342 days.

(21) Appl. No.: 11/760,471

(22) Filed: Jun. 8, 2007

(65) Prior Publication Data

US 2007/0295988 A1 Dec. 27, 2007

(30) Foreign Application Priority Data

Jun. 26, 2006 (JP) ............................. 2006-175571

(51) Int. Cl.
*H01L 29/744* (2006.01)
(52) U.S. Cl. ............... 257/147; 257/139; 257/E29.212
(58) Field of Classification Search ................ 257/347, 257/349, 365, 147, 139
See application file for complete search history.

(56) References Cited

U.S. PATENT DOCUMENTS

| | | | |
|---|---|---|---|
| 4,020,830 A | 5/1977 | Johnson et al. | 128/2 E |
| 4,180,771 A | 12/1979 | Guckel | 324/71 |
| 5,827,482 A | 10/1998 | Shieh et al. | 422/82.02 |
| 6,833,059 B2 | 12/2004 | Kawarada | 204/403.01 |
| 2006/0068532 A1* | 3/2006 | Schuele et al. | 438/149 |
| 2006/0079035 A1* | 4/2006 | Eguchi et al. | 438/155 |
| 2006/0262589 A1 | 11/2006 | Hirai et al. | 365/96 |

FOREIGN PATENT DOCUMENTS

| JP | 11-514748 A | 12/1999 |
|---|---|---|
| JP | 3313696 | 5/2002 |

* cited by examiner

*Primary Examiner*—Jerome Jackson, Jr.
*Assistant Examiner*—Dale Page
(74) *Attorney, Agent, or Firm*—Fitzpatrick, Cella, Harper & Scinto

(57) ABSTRACT

A sensor includes a first gate electrode, a second gate electrode, a semiconductor layer, a gate-insulating layer, a source electrode, a drain electrode, and a sensing portion including an accommodating part and a receiving layer. The first and second gate electrodes are opposed to each other with the sensing portion, the semiconductor layer, and the gate-insulating layer therebetween. One surface of the semiconductor layer is in contact with a surface of the sensing portion, and another surface of the semiconductor layer is in contact with the gate-insulating layer. A surface of the gate-insulating layer is in contact with the second gate electrode. The first gate electrode and the receiving layer are opposed to each other with the accommodating part therebetween. The source and drain electrodes are in contact with the semiconductor layer.

7 Claims, 9 Drawing Sheets

DUAL-GATE SENSOR

BACKGROUND OF THE INVENTION

1. Field of the Invention

The present invention relates to a sensor using a field effect transistor (FET).

2. Description of the Related Art

Japanese Patent No. 3,313,696 (Patent Document 1) discloses a chemical sensor using an FET, and U.S. Pat. No. 4,180,771 (Patent Document 2) discloses a chemical sensor in which an FET and a reference electrode are combined. However, the related arts described above have some problems, which will be described below in detail.

FIG. 1 is a schematic diagram showing a sensor using an FET having one gate electrode, which is described in Patent Document 1. The device has a source electrode 5, a drain electrode 6, an insulating film 7, a target substance 9, and a non-target substance 10. When a voltage is applied to a gate electrode 2 shown in FIG. 1, a channel 13 is formed in an upper layer region of a semiconductor layer 4. In such a case, since the channel 13 and a receiving layer 8 are in close proximity to each other, it is expected that measurement can be performed with high sensitivity. However, because of the close proximity between the channel 13 and the receiving layer 8, carrier movement occurs from the channel 13 to a sample solution 11. That is, leakage current occurs from the channel 13 to the sample solution 11. Consequently, it is difficult to perform electrical measurement accurately.

FIG. 2 is a schematic diagram showing another sensor including one gate electrode and a reference electrode, which is described in Patent Document 2. In the sensor shown in FIG. 2, since the electrical potential of a sample solution 11 can be kept constant by a reference electrode 12, it is believed to be possible to perform stable electrical measurement. However, since a channel 13 is formed by applying a voltage to a gate electrode 200 having a gate-insulating layer 3 thereon, the channel 13 is formed in a lower layer region of a semiconductor layer 4 at a point distant from a receiving layer 8. Consequently, it is difficult to perform electrical measurement with high sensitivity.

SUMMARY OF THE INVENTION

The present invention provides a sensor in which the distance between a channel and a receiving layer is small, and it is possible to inhibit carriers from moving from the channel to a sample solution, namely, a sensor in which highly sensitive detection and stable electrical property measurement can be realized.

An aspect of the present invention relates to a sensor including at least a first gate electrode, a second gate electrode, a semiconductor layer, a gate-insulating layer, a source electrode, a drain electrode, and a sensing portion including an accommodating part for accommodating an analyte and a receiving layer. The first gate electrode and the second gate electrode are opposed to each other with the sensing portion, the semiconductor layer, and the gate-insulating layer therebetween. One surface of the semiconductor layer is in contact with a surface, on which the receiving layer is present, of the sensing portion. Another surface of the semiconductor layer is in contact with the gate-insulating layer. A surface of the gate-insulating layer, which is different from a surface in contact with the semiconductor layer, is in contact with the second gate electrode. The first gate electrode and the receiving layer are opposed to each other with the accommodating part therebetween. The source electrode and the drain electrode are in contact with the semiconductor layer.

The source electrode and the drain electrode can be present on the first gate electrode side of the semiconductor layer, each of the source electrode and the drain electrode being not in contact with the sensing portion, wherein an insulating film is disposed between the source electrode and the sensing portion and between the drain electrode and the sensing portion.

The semiconductor layer can be made of an organic semiconductor.

The receiving layer and the surface of the semiconductor layer can be bonded to each other by chemical bonding.

Another aspect of the present invention relates to a method for driving a sensor which includes at least a first gate electrode, a second gate electrode, a semiconductor layer, a gate-insulating layer, a source electrode, a drain electrode, and a sensing portion including an accommodating part for accommodating an analyte and a receiving layer, wherein the first gate electrode and the second gate electrode are opposed to each other with the sensing portion, the semiconductor layer, and the gate-insulating layer therebetween, one surface of the semiconductor layer is in contact with a surface, on which the receiving layer is present, of the sensing portion, another surface of the semiconductor layer is in contact with the gate-insulating layer, a surface of the gate-insulating layer, which is different from a surface in contact with the semiconductor layer, is in contact with the second gate electrode, the first gate electrode and the receiving layer are opposed to each other with the accommodating part therebetween, and the source electrode and the drain electrode are in contact with the semiconductor layer, the method including, at least, placing an analyte in the sensing portion, applying a voltage equal to or lower than a threshold voltage to the second gate electrode, applying a voltage higher than the threshold voltage to the first gate electrode to form a channel in a region of the semiconductor layer in contact with the surface, on which the receiving layer is present, of the sensing portion, and measuring an electrical property of the channel.

Further features of the present invention will become apparent from the following description of exemplary embodiments with reference to the attached drawings.

DESCRIPTION OF THE EMBODIMENTS

The present invention relates to a sensor having two gate electrodes (i.e., a dual-gate sensor). Embodiments of the invention will be described below.

Figure 1:
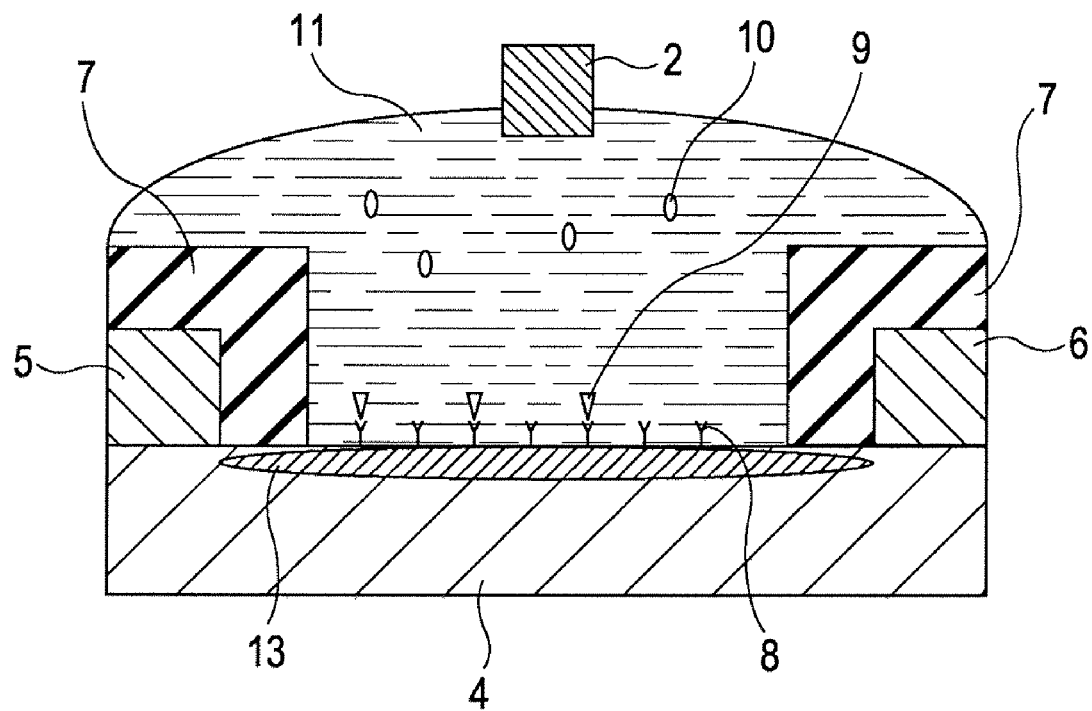
FIG. 1 is a schematic diagram of a known sensor using an FET having one gate electrode.
Figure 2:
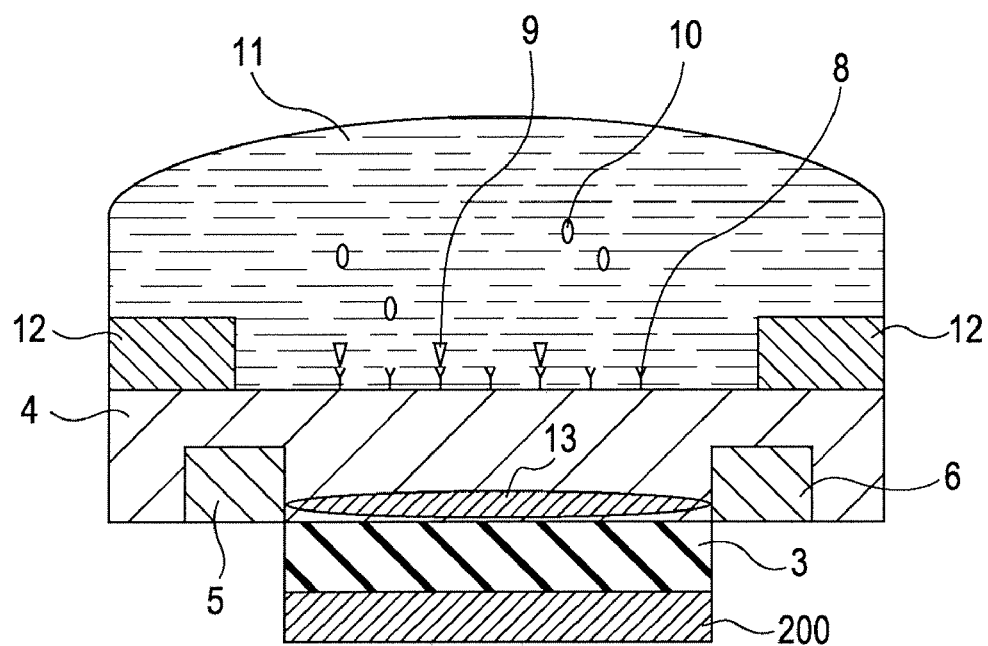
FIG. 2 is a schematic diagram of a known sensor using an FET having one gate electrode and a reference electrode.
Figure 3:
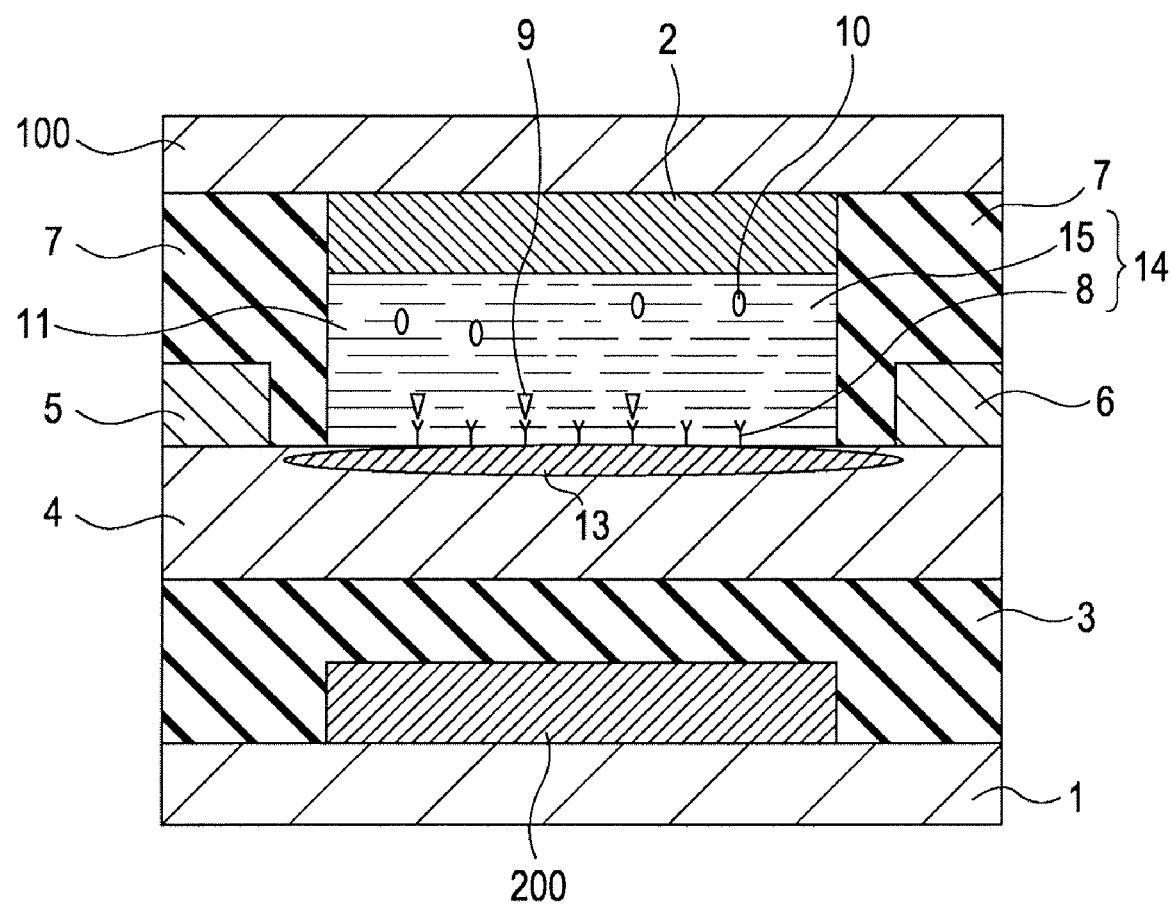
FIG. 3 is a schematic diagram of a dual-gate sensor according to an example of an embodiment of the present invention.
Figure 4:
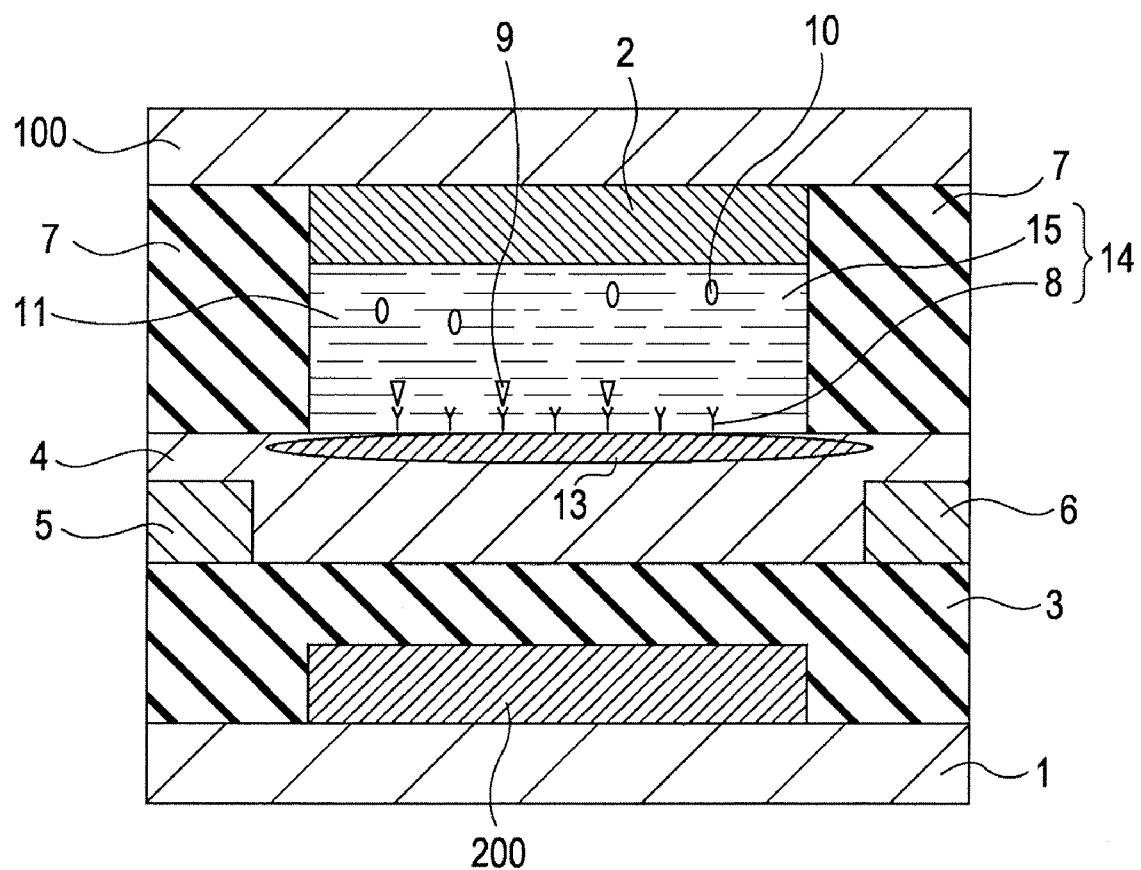
FIG. 4 is a schematic diagram of a dual-gate sensor according to another example of the embodiment of the present invention.
Figure 5:
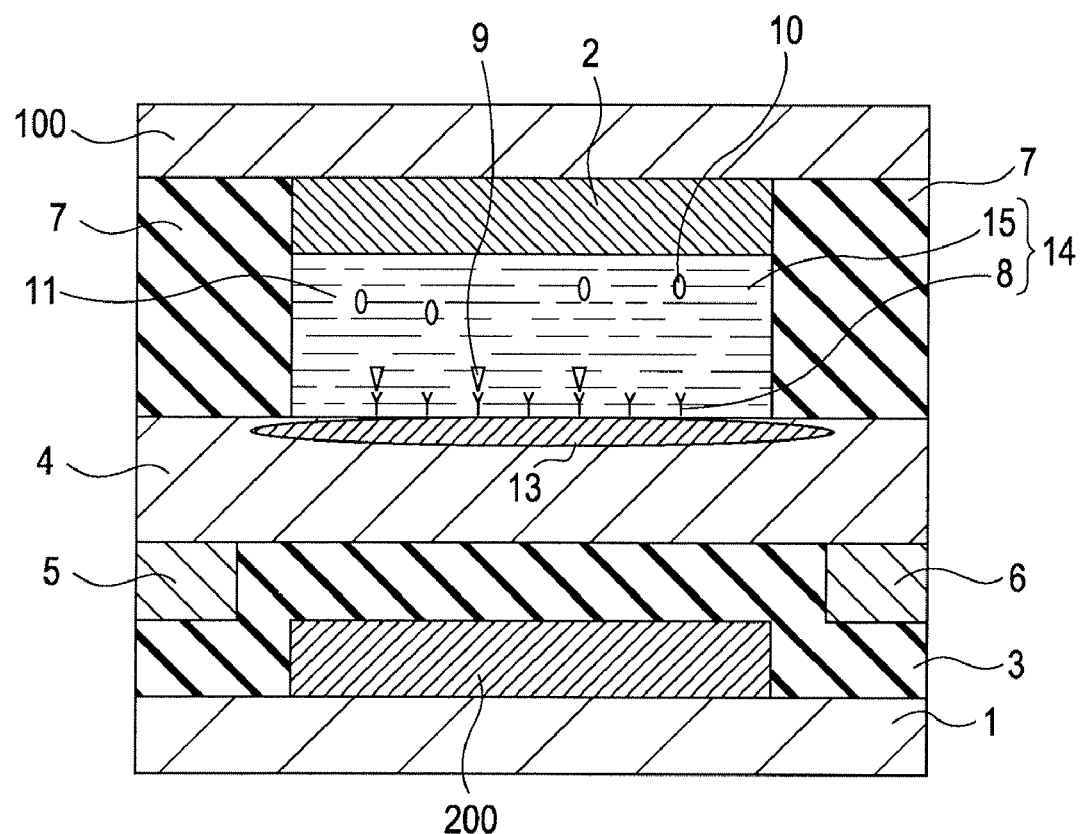
FIG. 5 is a schematic diagram of a dual-gate sensor according to another example of the embodiment of the present invention.

FIGS. 3 to 5 show examples of a dual-gate sensor according to one embodiment, and in all of the drawings, the same elements are represented by the same reference numerals, wherein duplication of description is avoided.

The dual-gate sensor according to the embodiment includes a substrate 1, a second gate electrode 200, a gate-insulating layer 3, a semiconductor layer 4, a source electrode 5, a drain electrode 6, an insulating film 7, a sensing portion 14 including a receiving layer 8 and an accommodating part 15, a first gate electrode 2, and a substrate 100. In the dual-gate sensor shown in each drawing, the accommodating part 15 is filled with a sample solution 11 which is an analyte.

In the dual-gate sensor according to this embodiment, by applying a voltage to the first gate electrode 2, a channel 13 can be formed in an upper layer region, which is in close proximity to the receiving layer 8, of the semiconductor layer 4. In addition, by applying a voltage to the second gate electrode 200, it is possible to inhibit carriers from moving from the channel 13 to the sample solution 11. That is, the channel 13 is formed in the region of the semiconductor layer 4 in close proximity to the receiving layer 8 by applying a voltage to the first gate electrode 2, and also leakage current is reduced by applying a voltage to the second gate electrode 200. Consequently, it is possible to perform stable measurement with high sensitivity.

Figure 6:
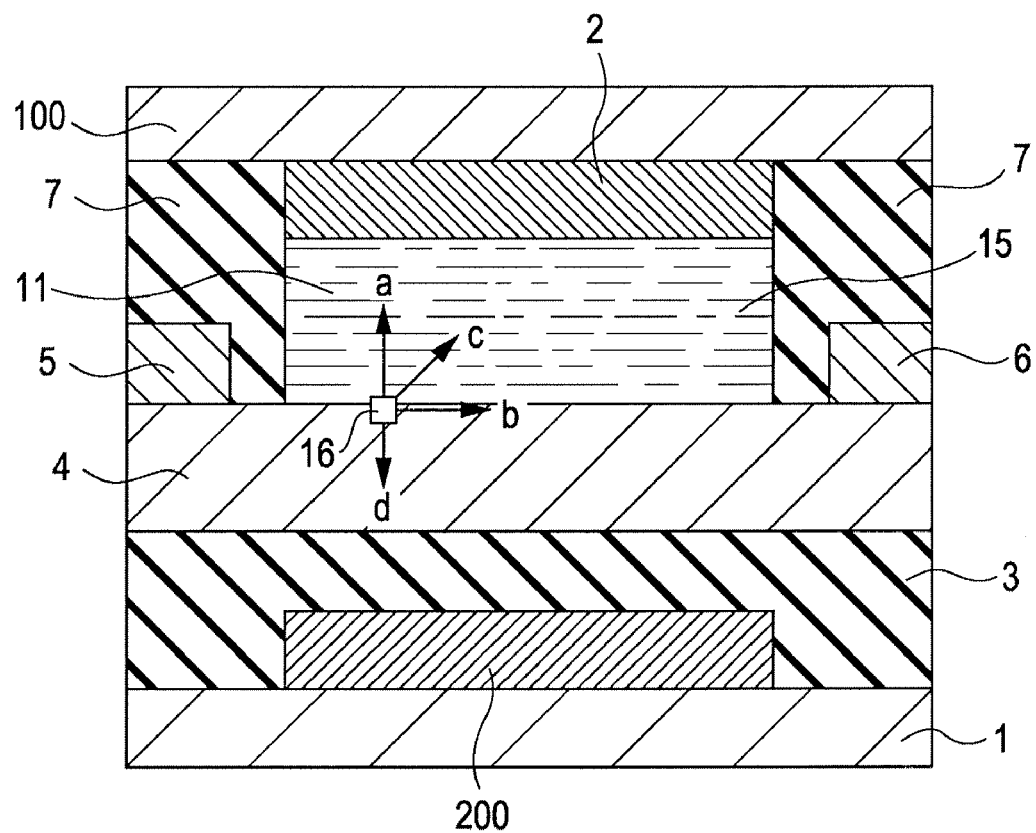
FIG. 6 is a schematic diagram illustrating forces applied to a carrier in the dual-gate sensor according to the embodiment of the present invention.

This will be described with reference to FIG. 6. FIG. 6 is a schematic diagram illustrating forces applied to a carrier when a voltage is applied to each electrode in the sensor shown in FIG. 3. Reference numeral 16 represents a carrier. Here, description will be made on the assumption that a negative voltage is applied to the first gate electrode 2, a negative voltage is applied to a drain electrode 6, a negative voltage is applied to the second gate electrode 200, a source electrode 5 is grounded, and the semiconductor layer 4 is made of a p-type semiconductor.

A Coulomb force a is applied to the carrier 16, in a direction from the semiconductor layer 4 to the first gate electrode 2, by means of the voltage applied to the first gate electrode 2. A Coulomb force b is applied to the carrier 16, in a direction from the source electrode 5 to the drain electrode 6, by means of the voltages applied to the source and drain electrodes. As a result of the forces a and b, a Coulomb force c is applied to the carrier 16. If the force a is large, the carrier moves into the sample solution 11, resulting in generation of an electric charge leaking out from the semiconductor layer 4 to the sample solution 11 (hereinafter for convenience referred to as a "leakage current from the semiconductor layer 4 to the sample solution 11"). Consequently, by adding a downward force, namely, by adding a Coulomb force d in a direction from the semiconductor layer 4 to the second gate electrode 200, the force which is applied to the carrier and directed from the sample solution 11 to the first gate electrode 2 is inhibited. Thus, it is possible to reduce generation of leakage current.

The individual elements constituting the sensors shown in FIGS. 3 to 5 will be described in detail below.

The sensor according to the embodiment of the present invention uses a transistor. Thus, the semiconductor layer 4 is a constituent element that allows a region of the semiconductor layer 4 in the vicinity of an interface with the receiving layer to function as the channel 13.

The semiconductor layer 4 may be composed of any one of an inorganic semiconductor material, an organic semiconductor material, and a hybrid of an inorganic semiconductor material and an organic semiconductor material. In particular, an organic semiconductor material is preferable because it can relatively easily immobilize a receptor. Examples of the inorganic semiconductor material that may constitute the semiconductor layer 4 include silicon and gallium arsenide. Examples of the organic semiconductor material include pentacene, phthalocyanine, perylene, porphyrin, polyaniline, polyvinylphenol, polythiophene, triarylamine, and fluorene. Examples of a hybrid of an inorganic semiconductor material and an organic semiconductor material include $(C_6H_5C_2H_4NH_3)_2SnI_4$. Furthermore, the thickness of the semiconductor layer 4 is preferably 100 nm or less. The reason for this is that if the semiconductor layer 4 is excessively thick, off-state current increases, resulting in a decrease in the sensitivity of the sensor.

Furthermore, the sensing portion 14 is a place where interaction takes place between a target substance 9 contained in the sample solution 11 and a capturing body of the receiving layer 8. In this embodiment, the combination of the accommodating part 15 and the receiving layer 8 is referred to as a sensing portion, the accommodating part 15 being surrounded by the first gate electrode 2, the semiconductor layer 4, and the insulating film 7 and being filled with the sample solution 11.

The receiving layer 8 includes a capturing body that specifically captures the target substance 9 detected by the sensor according to the embodiment. In this embodiment, examples of the interaction between the target substance that can be detected by the sensor and the capturing body include protein-protein interactions, such as antigen-antibody reactions, amino acid-protein interactions, enzyme-substrate reactions, RNA-protein interactions, DNA-DNA interactions, and complexation reactions. Therefore, in this embodiment, examples of the target substance that is detected by the sensor include proteins, such as antigens and antibodies, amino acids, enzymes, RNA, DNA, sugars, ions, and complexing molecules. The capturing body can be appropriately selected according to the target substance. Here, the receiving layer 8 including the capturing body is not limited to a layered structure, but may be a film containing a capturing body, such as an ion-exchange membrane or an ion-doped film. Furthermore, since the capturing body can specifically capture the target substance, even if the sample solution 11 contains a substance other than the target substance (i.e., a substance 10 other than the target substance shown in FIGS. 3 to 5), measurement can be performed qualitatively or quantitatively.

The accommodating part 15, which is filled with the sample solution 11, plays a role in providing a place for interaction between the target substance 9 in the sample solution 11 and the capturing body in the receiving layer 8 when the accommodating part 15 is filled with the sample solution 11, and also functions as a resistor between the first gate electrode 2 and the receiving layer 8. The dielectric constant of the sample solution is preferably in a range of 60 to 90, and more preferably in a range of 70 to 90, at a sample solution temperature of 25° C.

In order to fill the accommodating part 15 with the sample solution 11, a method may be employed in which the sample solution 11 is kept in the accommodating part, or a method may be employed in which the sample solution 11 passes through the accommodating part 15. In the latter case, the accommodating part 15 serves as a passage for the sample solution 11.

Furthermore, the semiconductor layer 4 and the capturing body of the receiving layer 8 can be bonded to each other by chemical bonding. In this embodiment, the term "chemical bonding" can refer to an ionic bond, a covalent bond, a coordinate bond, a metallic bond, and a hydrogen bond. In order to achieve chemical bonding, for example, a method may be used in which bonding is achieved by means of dehydration involving, for example, an amino group, a carboxyl group, or a hydroxyl group. Here, a method may also be used in which molecules having active groups for immobilizing the capturing body are immobilized on the surface of the semiconductor layer 4 in advance, and then the active groups are bonded to the capturing body so that the capturing body is immobilized on the surface of the semiconductor layer 4. Furthermore, in order to prevent nonspecific adsorption of substances other than the target substance 9 on the surface of the semiconductor layer 4, an area of the surface of the semiconductor layer 4 other than the area in which the capturing body is present may be coated with a blocking agent.

The source electrode 5 and the drain electrode 6 may be formed by vapor deposition, coating, nanoimprinting, or the like. The source electrode 5 and the drain electrode 6 may be formed at positions shown in any of FIGS. 3 to 5. In any case, since the channel 13 is formed by applying a voltage to the first gate electrode 2, the channel 13 is formed in the upper layer region of the semiconductor layer 4 as shown in FIGS. 3 to 5.

When the source electrode 5 and the drain electrode 6 are formed at positions that can be in contact with the sample solution 11, the insulating film 7 is disposed in order to prevent a current from flowing directly from the source electrode 5 to the drain electrode 6 through the sample solution 11. Consequently, the insulating film 7 is formed so as to cover the portions of the source electrode 5 and the drain electrode 6 that can be in contact with the sample solution 11, and so that the semiconductor layer 4 is in contact with the receiving layer 8 and the sample solution 11. Since the insulating film 7 is provided to prevent leakage current, the insulating film 7 is preferably composed of a material that does not transmit gas, liquids, ions, and the like. For example, parylene is used for the insulating film 7.

A voltage for forming the channel 13 is applied to the first gate electrode 2. The first gate electrode 2 is formed on the substrate 100 in advance, and the substrate 100 is arranged such that the surface provided with the first gate electrode 2 lies adjacent to the sensing portion 14 to fabricate a dual-gate sensor. As such a first gate electrode 2, an electrode made of a material that is chemically stable with respect to the solution is used. Among electrodes made of such a material, in particular, use of a gold electrode, a platinum electrode, a silver/silver chloride electrode, or a standard hydrogen electrode is preferable. Furthermore, any substrate that has a function of supporting the first gate electrode 2 can be used as the substrate 100. Preferably, the substrate 100 is made of a plastic having excellent impact resistance.

A voltage is applied to the second gate electrode 200 for the purpose of reducing the current that leaks from the semiconductor layer 4 into the sample solution 11 under the influence of the voltage applied to the first gate electrode 2. Consequently, in order to effectively reduce the leakage current under the influence of the voltage applied to the first gate electrode 2, the second gate electrode 200 is disposed so as to be opposed to the first gate electrode 2 with the semiconductor layer 4 and the gate-insulating layer 3 therebetween. Such a second gate electrode 200 may be disposed on the substrate 1. Alternatively, when the substrate 1 is made of an electrically conductive material, the substrate 1 may assume the function of the second gate electrode 200. Here, the substrate 1 has a function of supporting the entire device. When the second gate electrode 200 is formed on the substrate 1, as the material for the second gate electrode 200, for example, gold, platinum, or the like is used. When the substrate 1 also functions as the second gate electrode 200, a doped silicon substrate or the like may be used.

The gate-insulating layer 3 serves as a gate-insulating layer for the second gate electrode 200. As the material for such a gate-insulating layer 3, for example, polyvinylphenol, polyimide, or the like is used.

A method for driving the dual-gate sensor according to this embodiment will now be described below.

First, the optimum voltage applied to the second gate electrode 200 is determined as follows. It is expected that as the voltage applied to the second gate electrode 200 is increased, the effect of reducing the leakage current from the channel 13 into the sample solution 11 is increased. However, when the voltage applied to the second gate electrode 200 is higher than the threshold voltage of the transistor in this embodiment, a channel is formed in a lower layer region of the semiconductor layer 4. Therefore, the voltage applied to the second gate electrode 200 is set equal to or lower than the threshold voltage. In particular, when the optimum voltage applied to the second gate electrode 200 is set equal to the threshold voltage, it is possible to minimize the leakage current while maintaining high sensitivity, which is desirable. In the present invention and in this specification, the term "threshold voltage" is defined as a maximum voltage at which a channel is not formed when a voltage is applied to the semiconductor layer with the sensing portion having the receiving layer being filled only with the buffer solution of the analyte in the device. That is, when the voltage is equal to or lower than the threshold voltage, a channel is not formed.

In order to more strictly determine the optimum voltage that minimizes the leakage current, a method is used in which the voltage applied to the first gate electrode 2 is set at a constant value, the voltage applied to the second gate electrode 200 is varied, the current flowing in the first gate electrode 2 is measured, and the voltage that minimizes the current flowing in the first gate electrode is determined as the optimum voltage. The reason for determining the optimum voltage by such a method will be described below. In the steady state in which the source electrode 5 is grounded, a voltage is applied to the drain electrode 6, and a voltage is applied to each of the first gate electrode 2 and the second gate electrode 200, substantially no current flows in the first gate electrode 2. If any, the current is very weak and can be ignored in comparison with the sensitivity of the sensor. This is because the first gate electrode 2 and the second gate electrode 200 form a capacitor. On the other hand, when a leakage current from the channel 13 into the sample solution 11 is generated, the leakage current reaches the first gate electrode 2, and thus a current flows in the first gate electrode. Consequently, the voltage that minimizes the current flowing in the first gate electrode corresponds to the optimum voltage that minimizes the leakage current.

Next, the sample solution 11 is placed in the sensing portion 14 including the receiving layer 8 in the absence of an applied voltage to the second gate electrode 200. The placement of the solution may be performed by a batch method or by a flow method using a microchannel.

Subsequently, the optimum voltage as a constant value is applied to the second gate electrode 200, and then by changing the voltage of the first gate electrode 2, a channel 13 is formed in a region of the semiconductor layer 4 in contact with the surface, on which the receiving layer 8 is present, of the sensing portion 14. Here, the "region of the semiconductor layer 4 in contact with the surface, on which the receiving layer 8 is present, of the sensing portion 14" is defined as a region of the semiconductor layer 4 extending to one third of the thickness of the semiconductor layer 4 from the interface with the surface, on which the receiving layer 8 is present, of the sensing portion 14. A change in an electrical property of the channel thus formed is measured. Note that the voltage applied to the first gate electrode 2 is higher than the threshold voltage. In the sensor according to this embodiment, a change in an electrical property (e.g., drain current or mobility) between the state in which the capturing body of the receiving layer 8 captures the target substance 9 and the state in which the capturing body does not capture the target substance 9 is measured. Thus, it is possible to determine the presence or absence of the target substance and to measure the concentration of the target substance by comparing the measured result with a calibration curve prepared in advance. Here, the electrical property value can be measured using a measurement system with a gauge unit, PC, analysis software, etc.

In the sensor according to this embodiment, it is also possible to form a differential pair electrically using a second transistor that is substantially the same as the transistor described above. In the measurement method using the differential pair, the current value of the transistor when the sample solution 11 is allowed to flow and the current value of the transistor when a buffer solution (i.e., a solution corresponding to the sample solution excluding only the target substance) only is allowed to flow are simultaneously measured, and a difference in the current value is defined as a sensing amount. It is also possible to integrate the sensor according to this embodiment into a card sensor chip.

EXAMPLES

Examples of the present invention will be described in detail below. It is of course to be understood that the present invention is not limited to the examples.

Example 1

A dual-gate sensor shown in FIG. 3 is fabricated. Gold is vapor-deposited on a plastic substrate 1 to form a second gold gate electrode 200. A solution containing a polyimide is applied by spin-coating on the second gate electrode 200, followed by drying, to form a gate-insulating layer 3 with a thickness of 800 nm. Tetrabenzoporphyrin is vapor-deposited with a thickness of 70 nm on the gate-insulating layer 3, and carboxyl group-containing tetrabenzoporphyrin is vapor-deposited thereon with a thickness of 10 nm to form a semiconductor layer 4. Subsequently, gold is vapor-deposited on the resulting semiconductor layer 4 to form a source electrode 5 and a drain electrode 6 such that the gate length (distance between the source electrode and the drain electrode) is 50 μm and the gate width is 3 mm. Furthermore, in order to prevent the source electrode 5 and the drain electrode 6 from being in contact with a sample solution 10, an insulating film 7 made of parylene is formed.

Next, bovine serum albumin (BSA), which is a capturing body, is dissolved at a concentration of 10 ng/ml in a 0.1 M phosphate buffer solution (PBS) with pH 7.6 to prepare a BSA solution. Then, carboxyl groups of the semiconductor layer 4 are converted to succinimide using water-soluble carbodiimide (WSC) and N-hydroxysuccinimide (NHS). The BSA solution prepared as described above is added dropwise to the surface of the semiconductor layer 4 which is composed of the tetrabenzoporphyrin, the carboxyl groups of which have been converted to succinimide, and thus the BSA antigen is immobilized on the surface of the semiconductor layer 4 to form a receiving layer 8. Finally, a 1 M ethanolamine-hydrochloric acid solution (pH 8.3) is added dropwise thereto to carry out a blocking treatment.

Subsequently, gold is vapor-deposited on a plastic substrate 100 to form a first gate electrode 2 on the surface thereof. The substrate 100 provided with the first gate electrode 2 is bonded to the other elements constituting a dual-gate sensor. Thus, a dual-gate sensor shown in FIG. 3 is obtained.

Subsequently, the optimum voltage to be applied to the second gate electrode 200 for the purpose of minimizing the leakage current from the channel 13 to the sample solution is determined.

The sensing portion 14 is filled with a 0.1 M phosphate buffer solution (PBS) with pH 7.6 using a microchannel. Then, the source electrode 5 is grounded, and a voltage of −20 V is applied to the drain electrode 6. A voltage of −10 V is applied to the first gate electrode 2. While varying the voltage applied to the second gate electrode 200 from 0 V to −5 V, which is the threshold voltage, the optimum voltage at which the current flowing in the first gate electrode is minimum is measured. Thus, the optimum voltage is set at −5 V.

After the optimum voltage is determined, a sample solution 11 is allowed to flow through the sensing portion 14 using a microchannel. Here, the sample solution 11 is a solution prepared by dissolving an anti-BSA antibody 9, which is a target substance, at a concentration of 10 ng/ml in a 0.1 M phosphate buffer solution (PBS) with pH 7.6.

Next, with the source electrode 5 being grounded, the drain electrode 6 being applied with −80 V, and the second gate electrode 200 being applied with −5 V, which is the optimum voltage, a voltage in a range of 0 to −80 V is applied to the first gate electrode 2 to measure an electrical property.

Furthermore, in the case where measurement is performed by changing the concentration of the sample solution, a 0.1 M glycine-hydrochloric acid buffer regenerant solution (pH 2.2) is allowed to flow through the sensing portion 14 for 3 minutes to dissociate the target substance from the capturing body. Then, the sensing portion is washed with a 0.1 M phosphate buffer solution (PBS) with pH 7.6. A sample solution 11 with a different concentration is allowed to flow in the same manner as that described above, and the electrical property is measured again.

Thus, a calibration curve is prepared, which shows a change in the electrical property when the concentration of the target substance is changed.

Next, measurement is performed in the same manner using a sample solution containing the target substance with an unknown concentration. By comparing the measured electrical property with the calibration curve, it is possible to measure the concentration of the target substance.

Furthermore, since the capturing body specifically bonds with the target substance, even when measurement is performed in the same manner using a sample solution containing a substance other than the target substance as shown in FIG. 3, it is possible to measure the concentration of the target substance.

Figure 7:
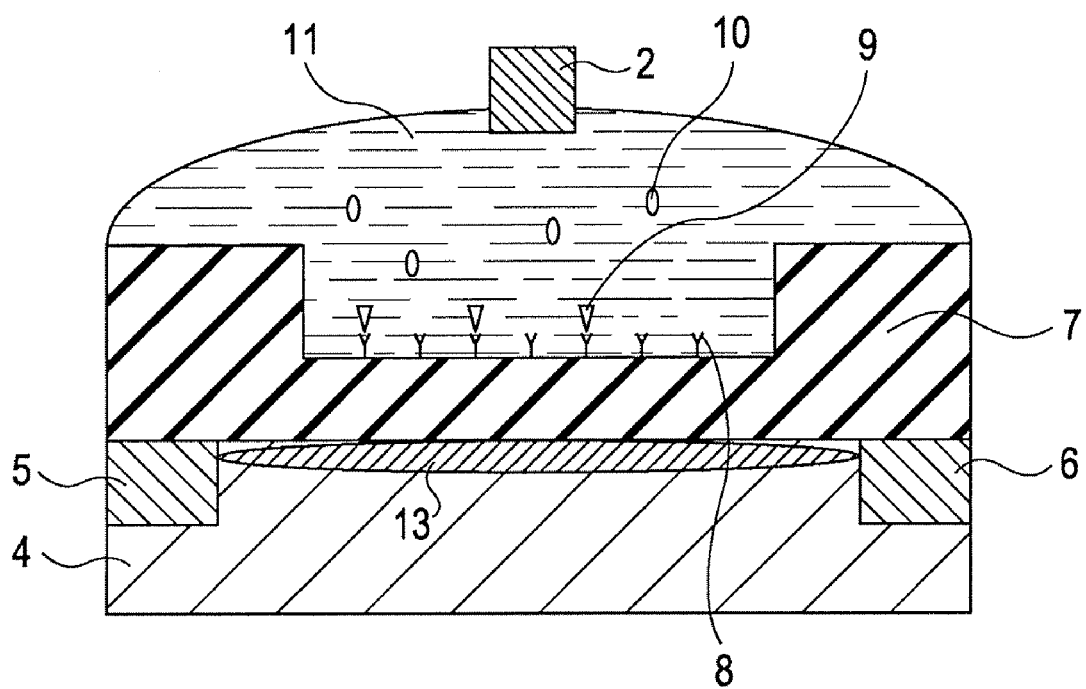
FIG. 7 is a schematic diagram illustrating a sensor using an FET having one gate electrode.
Figure 8:
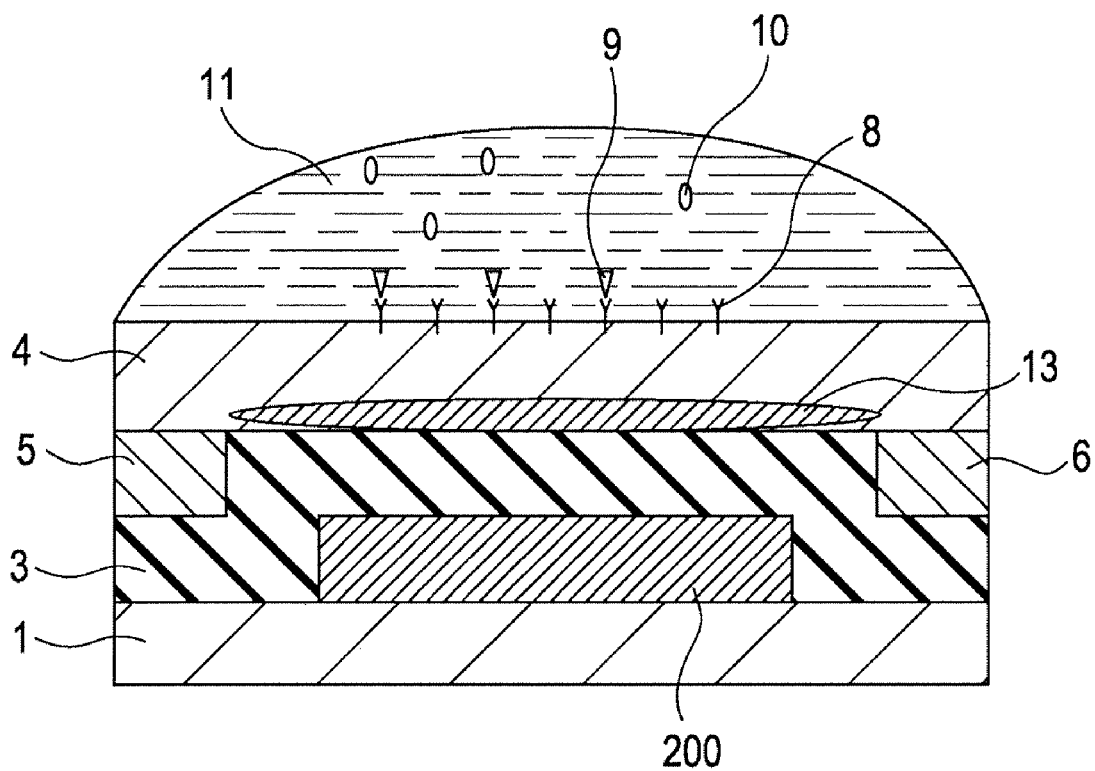
FIG. 8 is a schematic diagram illustrating another sensor using an FET having one gate electrode.
Figure 9:
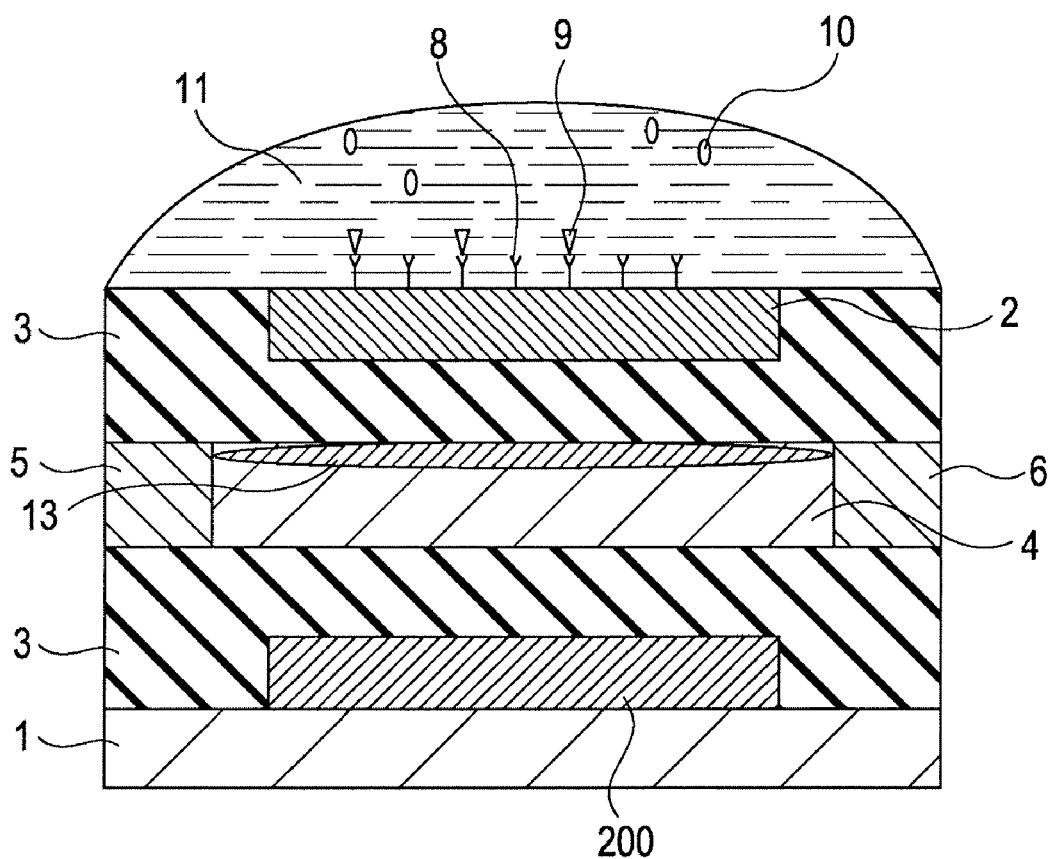
FIG. 9 is a schematic diagram illustrating a sensor using an FET having two gate electrodes.

As described above, by using the sensor according to any of the embodiments of the present invention, it is possible to perform electrical property measurement stably with high sensitivity compared with the sensor having a structure shown in any of FIGS. 7 to 9.

In a sensor having the structure shown in FIG. 7, by disposing an insulating layer 7 between a channel 13 and a receiving layer 8, carrier movement from the channel 13 to a sample solution 11 is inhibited. However, the sensitivity is degraded because the channel 13 and the receiving layer 8 are separated from each other.

In a sensor having the structure shown in FIG. 8, since a channel 13 is formed in a lower layer region of a semiconductor layer 4, the channel 13 and the receiving layer 8 are separated from each other, and the sensitivity is degraded.

In a sensor having the structure shown in FIG. 9, since a channel 13 is separated from a receiving layer 8, it is difficult to perform measurement with high sensitivity.

Consequently, by using the present invention, it is possible to provide a sensor capable of performing electrical property measurement stably and with high sensitivity.

While the present invention has been described with reference to exemplary embodiments, it is to be understood that the invention is not limited to the disclosed embodiments. The scope of the following claims is to be accorded the broadest interpretation so as to encompass all modifications, equivalent structures and functions.

This application claims the benefit of Japanese Application No. 2006-175571 filed Jun. 26, 2006, which is hereby incorporated by reference herein in its entirety.

What is claimed is:

1. A sensor comprising:
   a first gate electrode;
   a second gate electrode;
   a semiconductor layer;
   a gate-insulating layer;
   a source electrode;
   a drain electrode; and
   a sensing portion including an accommodating part for receiving a sample solution; and
   a receiving layer, the receiving layer being arranged on a surface of the sensing portion,
   wherein the first gate electrode and the second gate electrode are opposed to each other with the sensing portion, the semiconductor layer, and the gate-insulating layer therebetween,
   wherein a first surface of the semiconductor layer is in contact with the surface of the sensing portion on which the receiving layer is arranged,
   wherein a second surface of the semiconductor layer is in contact with a first surface of the gate-insulating layer,
   wherein a second surface of the gate-insulating layer, which is different from the first surface in contact with the semiconductor layer, is in contact with the second gate electrode,
   wherein the first gate electrode and the receiving layer are opposed to each other with the accommodating part of the sensing portion positioned therebetween, and
   wherein the source electrode and the drain electrode are in contact with the semiconductor layer.

2. The sensor according to claim 1, wherein the source electrode and the drain electrode are present on the first gate electrode side of the semiconductor layer, each of the source electrode and the drain electrode is not in contact with the sensing portion, and an insulating film is disposed between the source electrode and the sensing portion and between the drain electrode and the sensing portion.

3. The sensor according to claim 1, wherein the semiconductor layer is made of an organic semiconductor.

4. The sensor according to claim 1, wherein the receiving layer and the first surface of the semiconductor layer are bonded to each other by chemical bonding.

5. A method for driving a sensor that includes a first gate electrode, a second gate electrode, a semiconductor layer, a gate-insulating layer, a source electrode, a drain electrode, and a sensing portion including an accommodating part for receiving a sample solution, and a receiving layer, the receiving layer being arranged on a surface of the sensing portion, wherein the first gate electrode and the second gate electrode are opposed to each other with the sensing portion, the semiconductor layer, and the gate-insulating layer therebetween, wherein a first surface of the semiconductor layer is in contact with the surface of the sensing portion on which the receiving layer is arranged, wherein a second surface of the semiconductor layer is in contact with a first surface of the gate-insulating layer, wherein a second surface of the gate-insulating layer, which is different from the first surface in contact with the semiconductor layer, is in contact with the second gate electrode, wherein the first gate electrode and the receiving layer are opposed to each other with the accommodating part of the sensing portion positioned therebetween, and wherein the source electrode and the drain electrode are in contact with the semiconductor layer, the method comprising:
   placing a sample solution in the accommodating part of the sensing portion;
   applying a voltage equal to or lower than a threshold voltage to the second gate electrode;
   applying a voltage higher than the threshold voltage to the first gate electrode to form a channel in a region of the semiconductor layer in contact with the surface of the sensing portion on which the receiving layer is arranged; and
   measuring an electrical property of the channel.

6. A sensor comprising:
   a source electrode and a drain electrode disposed with a space therebetween;
   a first gate electrode;
   a second gate electrode;
   a semiconductor layer having a receiving layer for receiving a target substance contained in a sample solution;
   a sensing portion for accommodating the sample solution;
   a gate insulating layer for insulating the semiconductor layer from the second gate electrode,
   wherein the second gate electrode is disposed in the space between the source electrode and the drain electrode, and
   wherein the first gate electrode is disposed so as to be opposed to the second gate electrode, and
   wherein the sensing portion includes at least the receiving layer and the first gate electrode.

7. A method for driving a sensor including: a source electrode and a drain electrode disposed with a space therebetween; a first gate electrode; a second gate electrode; a semiconductor layer having a receiving layer for receiving a target substance contained in a sample solution; a sensing portion for accommodating the sample solution; and a gate insulating for insulating the semiconductor layer from the second gate electrode, wherein the second gate electrode is disposed in the space between the source electrode and the drain electrode, wherein the first gate electrode is disposed so as to be opposed to the second gate electrode, and wherein the sensing portion includes at least the receiving layer and the first gate electrode, the method comprising:
   inserting the sample solution into the sensing portion;
   applying a voltage equal to or lower than a threshold voltage to the second gate electrode;
   applying a voltage higher than the threshold voltage to the first gate electrode; and
   measuring a change of a drain current or a change of mobility of the semiconductor layer.

* * * * *